United States Patent [19]
Alpert

[11] Patent Number: 5,997,302
[45] Date of Patent: *Dec. 7, 1999

[54] METHOD FOR THE FORMATION OF DENTAL RESTORATIONS FROM CONDENSABLE COMPOSITES

[75] Inventor: Bruce Alpert, Madison, Conn.

[73] Assignee: Jeneric Pentron Incorporated, Wallingford, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 09/023,643

[22] Filed: Feb. 13, 1998

Related U.S. Application Data

[60] Provisional application No. 60/066,799, Nov. 26, 1997.

[51] Int. Cl.$^6$ ........................................................ A61C 5/10
[52] U.S. Cl. ........................ 433/223; 433/215; 433/226; 249/155; 425/2
[58] Field of Search ...................................... 433/223, 215, 433/218, 228.1, 226, 214; 249/155; 425/2; 75/228; 29/160.6; 428/212

[56] References Cited

U.S. PATENT DOCUMENTS

| | | |
|---|---|---|
| 2,477,268 | 7/1949 | Saffir . |
| 2,514,076 | 7/1950 | Kelly . |
| 3,066,112 | 11/1962 | Bowen . |
| 3,096,144 | 7/1963 | Wainer et al. . |
| 3,328,230 | 6/1967 | Levecque et al. . |
| 4,215,033 | 7/1980 | Bowen . |
| 4,381,918 | 5/1983 | Ehrnford . |
| 4,392,828 | 7/1983 | Ehrnford ............................. 433/217 |
| 4,427,799 | 1/1984 | Orlowski et al. . |
| 4,500,657 | 2/1985 | Kumar . |
| 4,514,174 | 4/1985 | Dougherty et al. . |
| 4,707,504 | 11/1987 | Walkowiak et al. . |
| 4,744,759 | 5/1988 | Bowen ................................. 433/228.1 |
| 4,793,809 | 12/1988 | Sigler et al. . |
| 4,892,481 | 1/1990 | Kopunek et al. . |
| 4,894,012 | 1/1990 | Goldberg et al. . |
| 4,952,530 | 8/1990 | Brosnan et al. ........................ 501/39 |

(List continued on next page.)

FOREIGN PATENT DOCUMENTS

| | | |
|---|---|---|
| 2 416 074 | 8/1979 | France . |
| 34 16 083 | 10/1985 | Germany . |
| WO 96 03090 | 2/1996 | WIPO . |

OTHER PUBLICATIONS

DentsplyCaulk, *SureFil™High Density Posterior Restorative Technical Manual*.

K. F. Leinfelder, DDS, MS; Mark B. Lyles, MS, DMD; and Ronald G. Ritsco, DMD, MS; *A New Polymer Rigid Matrix Material;*78 vol. 24, No. 4, Sep. 1996.

*Primary Examiner*—John J. Wilson
*Assistant Examiner*—Pedro Philogene
*Attorney, Agent, or Firm*—Cantor Colburn LLP

[57] ABSTRACT

A method and kit is presented, wherein a prepared tooth cavity is etched; treated with a primer/adhesive which is cured; treated with a flowable composite and cured; and then filled with a condensable composite, using techniques and instruments developed for use with amalgams. Such techniques include transferring the composite with an amalgam carrier, and shaping and packing the composite with an amalgam plugger. The dental restoration may optionally be further etched and sealed. The kit comprises at least a condensable composite and an amalgam carrier. The condensable composite is further provided in premeasured amounts, that is, in amounts of one spill, two spills, or three spills. In another embodiment, the kit further comprises a flowable composite material, and in still another embodiment, the kit further comprises a flowable composite material and dispenser, an etchant, a primer/adhesive, a plugger, and brush tips. The kit is especially useful in forming posterior dental restorations that are aesthetic, strongly-bonded, and wear-resistant. The restorations have negligible shrinkage upon polymerization.

21 Claims, 2 Drawing Sheets

U.S. PATENT DOCUMENTS

| | | |
|---|---|---|
| 4,997,373 | 3/1991 | Yanaka et al. . |
| 5,030,093 | 7/1991 | Mitnick ................................... 433/215 |
| 5,078,596 | 1/1992 | Carberry et al. . |
| 5,081,164 | 1/1992 | Lai . |
| 5,084,491 | 1/1992 | Kerby . |
| 5,118,296 | 6/1992 | Eldred ..................................... 433/223 |
| 5,266,609 | 11/1993 | Hall et al. . |
| 5,378,737 | 1/1995 | Jacobs et al. . |
| 5,549,123 | 8/1996 | Okuyama et al. . |
| 5,621,035 | 4/1997 | Lyles et al. .............................. 524/404 |
| 5,676,745 | 10/1997 | Kelly et al. . |
| 5,690,490 | 11/1997 | Cannon et al. ......................... 433/226 |
| 5,730,600 | 3/1998 | Shoher et al. .......................... 433/223 |
| 5,788,499 | 8/1998 | Hoffman ................................. 433/226 |
| 5,816,805 | 10/1998 | Cheetham ................................. 433/90 |
| 5,827,063 | 10/1998 | Greenstein .............................. 433/223 |

METHOD FOR THE FORMATION OF DENTAL RESTORATIONS FROM CONDENSABLE COMPOSITES

CROSS REFERENCE TO RELATED APPLICATIONS

This application claims priority to Provisional No. 60/066,799 filed as METHOD AND KIT FOR THE FORMATION OF DENTAL RESTORATIONS FROM CONDENSABLE COMPOSITES, filed Nov. 26,1997 by Bruce Alpert.

BACKGROUND OF THE INVENTION

1. Field of the Invention

This invention relates to dental restorations. In particular, this invention relates to a method and kit for the formation of dental restorations from condensable composites that have the feel of an amalgam.

2. Brief Description of the Related Art

Dental restorative materials include materials used to repair damaged teeth or to replace missing teeth. Conventionally, teeth are treated for decay by removing the decayed material grinding, and then replacing the decayed tooth portion with a dental restorative material. One commonly-used restorative material is an alloy of silver mixed with mercury, often referred to as dental amalgam.

Dentists and dental technicians have become accustomed to working with amalgam, which allows the dentist or dental technician to restructure and reshape the tooth surface by packing and molding the amalgam material. The characteristic of amalgam that allows such packing and molding is referred to as condensability. The condensability of amalgam is largely related to the ability of such material to respond to force applied in directions other than the direction of the applied force. This permits the application of a downward pressure of a dental tool to cause such material to respond laterally and conform to a lateral mold. During the condensation process mercury is forced from the amalgam and removed by mopping such that the mercury content of the amalgam content is actually reduced.

While well-suited for its intended purposes, and despite its various advantages, amalgam, has certain shortcomings regarding its cosmetic appearance and durability.

Dentists have accordingly looked for alternatives to amalgam, and in recent years a variety of filled polymeric materials have become available which are often referred to as composites. Dental composites are compatible with enamel and dentine, may be colored to match the surrounding dentition, and posses high durability. Dental composites most commonly comprise reinforcing inorganic fillers in the form of particulates, bound together by a polymeric matrix.

The polymeric matrix may be comprised of an acrylic or epoxy resin or other types of carbon-based polymers. Examples of polymeric materials (resins) suitable for use as dental composites are set forth in U.S. Pat. Nos. 3,066,112, U.S. Pat. No. 3,179,623, and U.S. Pat. No. 4,744,759 to Bowen, all of which are herein incorporated by reference. Fillers for dental composites include finely divided solids such as silica, glass, zirconium, aluminum oxide, crystalline quartz, glass beads, or mixtures of glass beads and quartz. Filler strength, content, shape, and size determine the physical and mechanical properties of the restoration material.

Again, while suitable for their intended purposes, composites comprising particulate fillers occasionally have some shortcomings when used as posterior restoration materials. A composite acceptable for posterior use must achieve a high filler loading in the polymeric matrix, and meet certain physical and mechanical properties. Some do not possess the wear resistance of conventional amalgams. Particulate-based composites also suffer from the disadvantage of the lack of the condensability found in conventional amalgams, and thus are not amenable to use with the techniques developed in connection with amalgams.

A new class of condensable composites has therefore been developed, comprising a polymeric matrix and various alternative forms of inorganic filler. Ehrnford in U.S. Pat. Nos. 4,381,918 and 4,392,828 describes bonded glass fiber matrices useful in dental composites, providing a composite generally possessing the feel and workability of amalgams. The fiber matrix also provided enhanced wear resistance. Brosnan et al. in U.S. Pat. No. 4,952,530 disclose a composite comprising a porous particulate filler that may be formed by methods generally used with amalgams. Lyles et al. in U.S. Pat. No. 5,621,035 further disclose a porous particulate material formed by sintering alumina and silica fibers in the presence of a flux such as boron. Finally, commonly-assigned U.S. application Ser. No. 08/951,414 to Jia et al. disclose that a composite having the feel and workability of amalgams may be made using densified, embrittled fibers. This material is commercially available under the trademark ALERT from Jeneric/Pentron, Inc., Wallingford, Conn. The increasing popularity of these composites having the feel and workability of amalgams has resulted in a need for methods for the efficient application of such composites, which result in dental restorations having the requisite strength, wear-resistance, and bonding to the restored tooth.

SUMMARY OF THE INVENTION

The above-discussed and other problems and deficiencies of the prior art are overcome or alleviated by the method and kit of the present invention, wherein a prepared tooth cavity is preferably etched; optionally treated with a primer/adhesive and then cured; optionally treated with a flowable composite and then cured; and then filled with a condensable composite, using techniques and instruments developed for use with amalgams. Such techniques include transferring the composite with an amalgam carrier, and shaping and packing the composite with an amalgam plugger. The amalgam carrier is preferable made of a high-impact plastic rather than metal. The dental restoration may optionally be further etched and sealed.

The kit of the present invention comprises at least a condensable composite and a high-impact plastic amalgam carrier. The condensable composite is further provided in premeasured amounts, that is, in amounts of one spill, two spills, or three spills. In another embodiment, the kit further comprises a flowable composite material, and in still another embodiment, the kit further comprises a flowable composite material and dispenser, an etchant, a primer/adhesive, a plugger, and brush tips. The kit is especially useful in forming posterior dental restorations that are aesthetic, strongly-bonded, and wear-resistant. The restorations have negligible shrinkage upon polymerization.

The above-discussed and other features and advantages of the present invention will be appreciated and understood by those skilled in the art from the following detailed description and drawings.

BRIEF DESCRIPTION OF THE DRAWINGS

Referring now to the drawings wherein like elements are numbered alike in the several FIGURES.

DESCRIPTION OF THE PREFERRED EMBODIMENT

Figure 1:
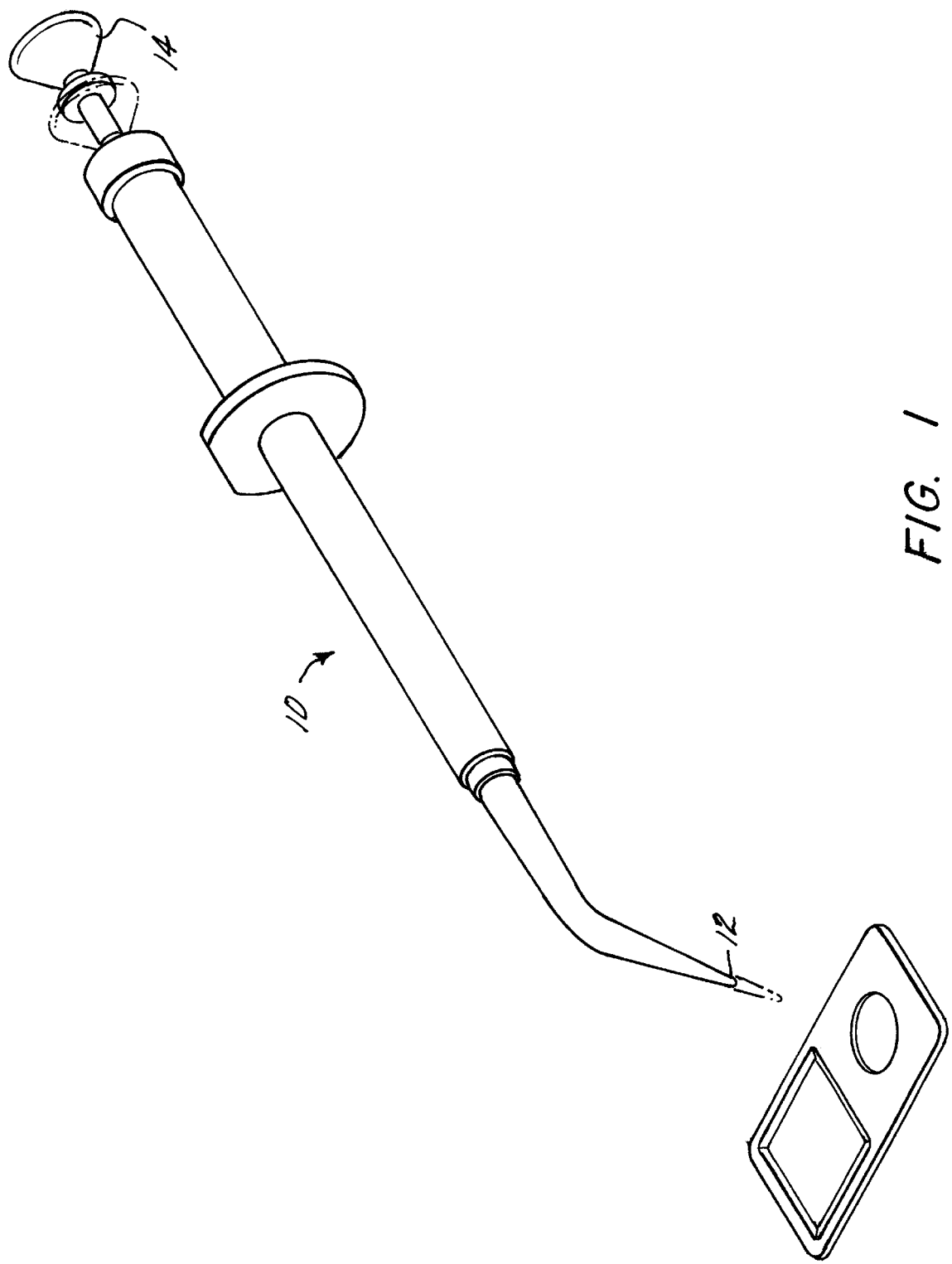
FIG. 1 is a plan view of an amalgam carrier suitable for use in the present invention.

The method according to the present invention is useful for making dental restorations such as fillings, facings, artificial teeth and the like. In order to provide a dental restoration having improved mechanical, physical and aesthetic properties, as well as improved properties related to clinical manipulation, the method is characterized by use of a condensable dental composite. As used hereinafter, "condensable" and "condensability" refer to the characteristic wherein the feel and workability of the composite is similar to that of amalgam, and thus amenable to application using clinical techniques similar to, or the same as, those developed for use with amalgam. Non-condensable composites are those known in the art which are to some extent thixotropic or flowable, and applied using a syringe or compule. "Condensable composites" are those which are not thixotropic and which do not flow, and which are applied using an amalgam carrier and amalgam plugger. As used herein, the terms "amalgam carrier" and "amalgam plugger" are inclusive of those instruments commonly used in connection with amalgam, but are also inclusive of instruments which may be suitable for the transfer and packing of condensable composites, but which have not heretofore or are not commonly used for carrying and packing of amalgam.

In accordance with the preferred method of the present invention, a prepared tooth cavity is etched; optionally treated with a primer/adhesive which is usually then cured; optionally treated with a flowable composite which is usually then cured; and then filled with a condensable composite, using techniques and instruments developed for use with amalgams. Such techniques include transferring the composite with an amalgam carrier, and shaping and packing the composite with an amalgam plugger. The amalgam carrier is preferably made of a high-impact plastic rather than metal. The dental restoration may optionally be further etched and sealed. Such dental restorations possess mechanical, physical and aesthetic properties which closely conform to the natural tooth structure. In addition, such restorations have negligible shrinkage upon polymerization.

Methods for preparing tooth cavities, e.g., for posterior fillings, are well-known in the art. Carbide friction-grip burs and cavo surface beveling i.e., Class V, are recommended in order to increase retention by greater enamel surface etching, and to minimize marginal leakage and ultimately improve marginal adaptability. It is further recommended that if a metal band is used, the inside of the metal band be lubricated using either wax or cavity varnish in order to prevent adhesion of the bonding materials to the band.

Acid etching of the enamel can be effected by applying an aqueous orthophosphoric acid solution or gel containing about 10–40%, preferably 37% by weight of orthophosphoric acid. The solution is applied to the enamel surface with a brush or small cotton pellet for about twenty seconds. After etching, the area should be washed well with water, and excess water should be removed either by blotting or by treating with a stream of air for about two seconds. The tooth surface should be left moist, as dry surfaces may result in poor bond strength and post-operative sensitivity. For bonding and sealing Class I, III, and V restorations, the enamel should, if possible, be conditioned at least one millimeter beyond the margin of the cavity preparation. For Class IV restorations, the etched area should be at least as wide as the tooth structure being replaced, but not less than two millimeters.

A thin layer of a primer, primer/adhesive, or adhesive is then applied to the tooth cavity. Primers, primer/adhesives, and adhesives and methods of application therefor are well-known in the art. A particularly suitable primer/adhesive is available under the trademark BOND-1 from Jeneric/Pentron, Inc., Wallingford, Conn. BOND-1 is an unfilled methacrylate-based primer/adhesive that provides strong bonds of up to about 31.0 Mpa, while also reducing tooth sensitivity. The bonding agent is preferably applied as two consecutive coats applied within ten seconds of each other, treated with air to remove solvent, and then polymerized by exposure to the visible light source for about 10 seconds, or until cure is substantially complete. An adhesive available under the trademark BOND-IT, available from Jeneric/Pentron, Inc., Wallingford, Conn. is also useful in the practice of the present invention.

A thin (0.5 to 1.0 mm) layer of a flowable dental composite material is then placed in the cavity by means known in the art, for example, a syringe or compule. A low-viscosity flowable resin is used in order to ensure that all surfaces of the cavity are wetted, and to provide microscopic adaptation of the condensable composite to the tooth cavity. A suitable low viscosity flowable composite resin is available under the trademark FLOW-IT from Jeneric/Pentron, Inc., Wallingford, Conn. The flowable composite is then light cured for about 40 seconds, or until cure is substantially complete.

Condensable composite resin is then placed and packed into the cavity using mechanical transfer and packing techniques. These techniques of mechanically packing a material into a tooth cavity are previously known to the dental profession in connection with dental amalgam, and have the well-known advantage in that they permit a close adaptation of To the filling material to the cavity walls. They further make it possible to give the restoration its final anatomic form before hardening, thereby avoiding time-consuming and difficult finishing work with rotating instruments.

It is to be understood that although the foregoing description is presently the preferred method of forming a dental restoration using a condensable composite, it is to be understood that various of the above-described steps may be omitted, or other steps known in the art may be added to the procedure. For example, other cavity preparation steps may be added, or the acid etch step may omitted. In another embodiment, the prepared cavity is acid etched; treated with a primer/adhesive or adhesive; and then the condensable composite is applied directly without use of the flowable composite. In still another embodiment, the prepared cavity is acid etched; treated with a flowable composite; and then the condensable composite is applied.

Thus, the condensable composite is first placed into the cavity using an amalgam carrier 10 as shown in FIG. 1. Preferably, the amalgam carrier is not metal or metal-surfaced, but rather a high-impact plastic or other material which will not result in discoloration of the composite. The carrier must be high-strength, that is, capable of withstanding the forces placed on the carrier by the dentist or technician while in use. Composite is loaded into hollow tip 12 of carrier 10 by pressing tip 12 directly into the composite without dragging or sliding tip 12 over the surface of the composite. The composite is ejected into the cavity by pressing plunger 14.

Figure 2:
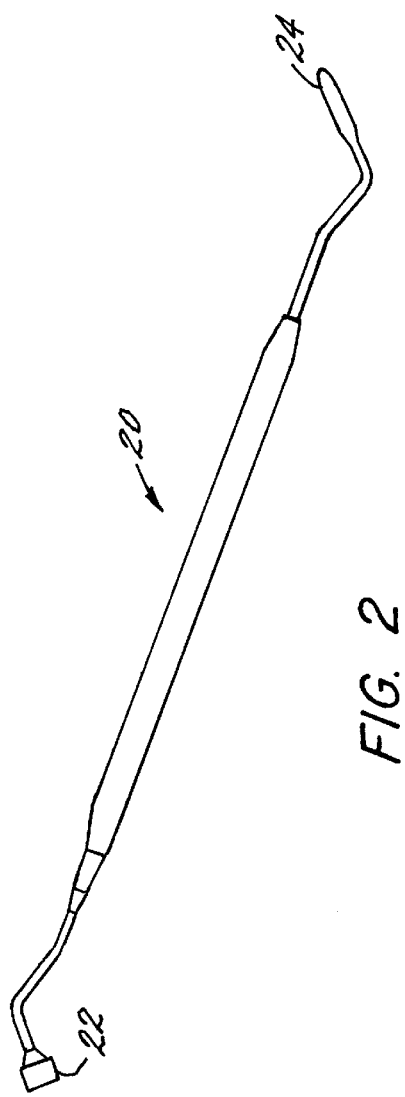
FIG. 2 is a plan view of an amalgam plugger suitable for use in the present invention.

The composite is then packed into the cavity using, e.g., the amalgam packer 22 and carver 24 shown generally as plugger 20 in FIG. 2. Suitable amalgam pluggers are known in the art, and available in a variety of forms. The application of force to the condensable composite in the presence of the flowable composite during packing results in microscopic adaptation of the filling to the tooth cavity, and thus enhanced bonding in the final restoration. After the cavity is filled, occlusal form is created by pushing the carver portion 24 of amalgam plugger 20. After the final form is achieved, the restoration is cured by suitable means.

A preferred condensable composite for use in the present method is available under the trademark ALERT from Jeneric/Pentron, Inc, Wallingford, Conn. Complete cure of ALERT by visible light to a 5 mm depth is achieved within about 40 seconds. Interproximal areas may be cured for an additional twenty seconds each. Where the preparation exceeds a depth of about 5.0 mm, an initial increment of condensable composite is placed, packed and light cured. A coat of a primer, primer/adhesive, or adhesive is then applied to the cured restoration, air dried as before, and light cured. A final increment of condensable composite is then placed and packed into the cavity, occlusal form is created, and the restoration cured.

Finally, the restoration is polished using conventional polishing materials and techniques, such as disks, composite polishing pastes, and polish-impregnated wheels and cups, and the like. Optionally, the surface of the restoration may be sealed to increase wear resistance and ensure the marginal integrity of the restoration. A suitable sealant is available under the trademark PROTECT-IT from Jeneric/Pentron, Inc., Wallingford, Conn. Application of this sealant requires first etching with an etchant such as phosphoric acid out to about 2 mm of enamel adjacent the restoration margin for about twenty seconds. The etchant is then removed by thorough washing. Sealant is then applied over the entire restoration surface, thinned using a jet of air, and cured. Subsequent polishing is usually not necessary.

The kit of the present invention comprises at least a condensable composite and a nonmetal-surfaced amalgam carrier such as that shown in FIG. 1. Amalgam carriers are well-known in the art, and other types of amalgam carrier may be suitable for use in the practice of the present invention. As mentioned above, use of metal or metal-surfaced carriers may result in discoloration of the condensable composite, and so their use is preferably avoided.

Figure 3:
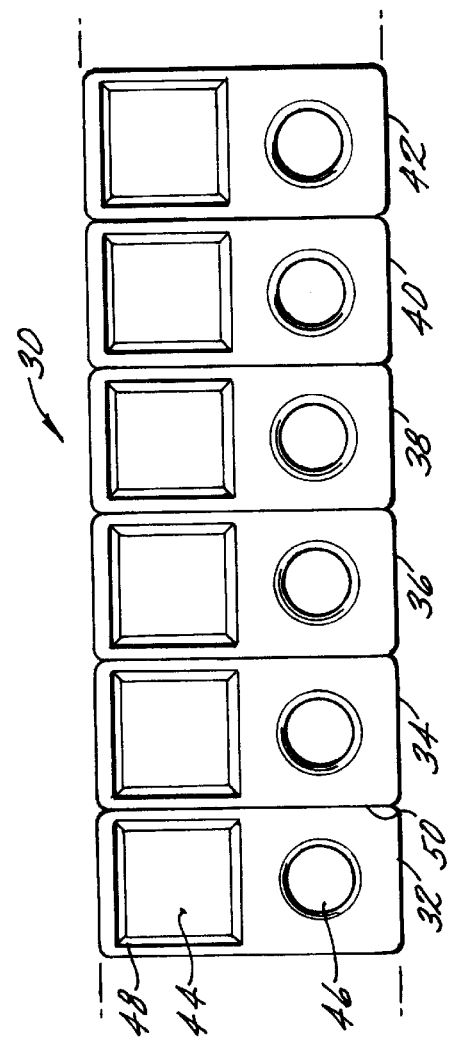
FIG. 3 is a plan view of a container for use in the present invention, comprising a plurality of tabs suitable for use with condensable composite.
Figure 4:
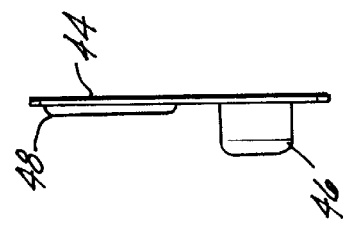
FIG. 4 is a side view of a container for use with the present invention, comprising a plurality of tabs suitable for use with condensable composite.

The condensable composite is preferably provided in premeasured amounts similarly to amalgam, that is, in amounts of one spill, two spills, or three spills. A container suitable for providing the premeasured amounts of condensable composite is shown in FIGS. 3 and 4. Container 30 generally comprises a plurality of tabs 32, 34, 36, 38, 40, 42 each tab having a holder portion 44 and a depression portion 46. Holder portion 44 optionally has an essentially square ridge portion 48 to aid the user in gripping and holding the tab, as illustrated in FIGS. 3 and 4. This optional ridge portion 48 may take the form of any shape to provide increased gripping capability. Depression portion 46 is sized so as to contain one spill, two spills, or three spills of condensable composite. Each tab 32, 34, 36, 38, 40, 42 is preferably detachably adhered to at least one additional tab, such that the tab is conveniently removed by the dentist or technician upon use. As shown in FIG. 3, for example, tab 32 is detachably adhered to tab 34 by score 50 extending longitudinally between tabs 32, 34. Each tab 32, 34, 36, 38, 40, 42 further comprises a removable cover made of foil or other flexible material to protect the composite during shipping and storage (not shown).

In another embodiment, the kit further comprises a flowable composite material, and in still another embodiment, the kit further comprises a flowable composite material and dispenser such as a syringe or compule, and at least one or all of an etchant, a primer/adhesive, a sealant, an amalgam plugger/carver, and brush tips. The elements of the kit are used as described above in connection with the method of the present invention. The kit is especially useful in forming posterior dental restorations that are aesthetic, strongly-bonded, and wear-resistant.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A method for forming a dental restoration, comprising
preparing a tooth cavity for receiving a dental restoration;
applying a flowable dental composite to the prepared tooth cavity so as to provide intimate contact between the surfaces of the cavity and the flowable dental composite;
forming the restoration with a condensable composite; and
curing the formed condensable composite restoration.

2. The method of claim 1, further comprising
treating the prepared tooth cavity with an etchant prior to applying the flowable composite composition.

3. The method of claim 1, further comprising treating the prepared tooth cavity with a primer, primer/adhesive, or adhesive composition or a combination thereof prior to applying the flowable composite composition.

4. The method of claim 3, wherein
the primer, primer/adhesive, adhesive composition or combination thereof is cured prior to application of the flowable composite compostion.

5. The method of claim 1, wherein the flowable composite composition is cured prior to forming the dental restoration with the condensable composite.

6. The method of claim 1, wherein
forming the restoration with the condensable composite comprises transferring the condensable composite to the cavity with an amalgam carrier;
packing the transferred condensable composite material with an amalgam plugger; and
curing the condensable composite.

7. The method of claim 1, further comprising
sealing the restoration with a sealant after cure of the condensable composite.

8. The method of claim 6, wherein
the amalgam carrier is formed of a high-impact plastic.

9. A dental restoration formed by the method of claim 1, wherein
the restoration is a filling, a veneer, a facing, or an artificial tooth.

10. A method for forming a dental restoration, comprising preparing a tooth cavity for receiving a dental restoration;

etching the cavity;

washing the etched cavity;

treating the etched, washed cavity with a primer, an adhesive/primer, an adhesive, or a combination thereof;

curing the primer, primer/adhesive, adhesive or combination thereof;

applying a flowable dental composite to the prepared tooth cavity as a thin layer so as to provide intimate contact between the surfaces of the cavity and the flowable dental composite;

curing the flowable dental composite;

forming the restoration with a condensable composite; and curing the formed condensable composite restoration.

11. The method of claim 10, further comprising sealing the cured condensable composite restoration with a sealant.

12. A dental restoration formed by the method of claim 10, wherein the restoration is a filling, a veneer, a facing, or an artificial tooth.

13. A method for forming a dental restoration, comprising preparing a tooth cavity for receiving a dental restoration;

applying a primer, primer/adhesive, primer and adhesive, or adhesive to the surfaces of cavity so as to provide intimate contact between the surfaces of the cavity and the a condensable dental composite;

forming the restoration with the condensable composite; and curing the formed condensable composite restoration.

14. The method of claim 13, further comprising treating the prepared tooth cavity with an etchant prior to applying the primer, primer/adhesive, primer and adhesive, or adhesive.

15. The method of claim 13, wherein the primer, primer/adhesive, primer and adhesive, or adhesive composition is cured prior to forming the dental restoration with the condensable composite.

16. The method of claim 13, further comprising treating the tooth cavity with a flowable composite after applying the primer, primer/adhesive, primer and adhesive, or adhesive, and prior to forming the dental restoration with the condensable composite, and prior to forming the dental restoration with the condensable composite.

17. The method of claim 13, wherein one or both of the primer, primer/adhesive, primer and adhesive, or adhesive and the the flowable composite composition is cured prior to forming the dental restoration with the condensable composite.

18. The method of claim 13, wherein forming the restoration with the condensable composite comprises transferring the condensable composite to the cavity with an amalgam carrier;

packing the transferred condensable composite material with an amalgam plugger; and curing the condensable composite.

19. The method of claim 13, further comprising sealing the restoration with a sealant after cure of the condensable composite.

20. The method of claim 18, wherein the amalgam carrier is formed of a high-impact plastic.

21. dental restoration formed by the method of claim 13, wherein the restoration is a filling, a veneer, a facing, or an artificial tooth.

* * * * *

UNITED STATES PATENT AND TRADEMARK OFFICE
CERTIFICATE OF CORRECTION

PATENT NO. : 5,997,302
DATED : December 7, 1999
INVENTOR(S) : Bruce Alpert

Page 1 of 1

It is certified that error appears in the above-identified patent and that said Letters Patent is hereby corrected as shown below:

Title Page:
Bibliographical page under Related to U.S. Application Data delete "60/066,799" and insert therefor -- 08/999,945 --

Column 1
Line 51, delete "posses" and insert therefor -- possesses --

Column 3
Line 2, and 4 delete the period "." and insert therefore a semi-colon -- ; -- in two places.
Line 7, delete the period "." and insert therefor -- ; and --

Column 4
Line 46 delete "To" between "of" and "the"

Column 7
Line 30 insert -- the -- between "of" and "cavity"
Line 3, and 32, delete "the" between "and" and "a"

Column 8
Lines 9, 10 and 11 delete ", and prior to forming the dental restoration with the condensible composite"
Line 34, insert -- A -- between "21." and "dental"

Signed and Sealed this

Twenty-first Day of August, 2001

Attest:

*Nicholas P. Godici*

NICHOLAS P. GODICI
*Attesting Officer*   *Acting Director of the United States Patent and Trademark Office*